US 6,747,051 B2

(12) United States Patent
Esser et al.

(10) Patent No.: US 6,747,051 B2
(45) Date of Patent: Jun. 8, 2004

(54) M-AMINO-PHENYLIMINO-IMIDAZOLIDINE DERIVATIVES FOR TREATING URINARY INCONTINENCE

(75) Inventors: Franz Esser, Ingelheim (DE); Pascale Pouzet, Ingelheim (DE); Hisato Kitagawa, Osaka (JP); Kenji Sakai, Hyogo (JP); Ikunobu Muramatsu, Fukui (JP)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 31 days.

(21) Appl. No.: 10/349,993

(22) Filed: Jan. 23, 2003

(65) Prior Publication Data

US 2003/0158420 A1 Aug. 21, 2003

Related U.S. Application Data

(63) Continuation of application No. 09/976,917, filed on Oct. 12, 2001, now Pat. No. 6,602,879.
(60) Provisional application No. 60/248,172, filed on Nov. 14, 2000.

(30) Foreign Application Priority Data

Oct. 14, 2000 (DE) .......................... 100 51 005

(51) Int. Cl.$^7$ .................. A61K 31/4168; C07D 233/44
(52) U.S. Cl. ..................................... 514/392; 548/331.5
(58) Field of Search ....................... 514/392; 548/331.5

(56) References Cited

U.S. PATENT DOCUMENTS 4,461,904 A * 7/1984 York, Jr. .................. 548/333.1
4,517,199 A * 5/1985 York, Jr. ...................... 514/392
4,587,257 A * 5/1986 DeSantis et al. ............ 514/392

* cited by examiner

Primary Examiner—Joseph K. McKane
Assistant Examiner—Kamal Saeed
(74) Attorney, Agent, or Firm—Robert P. Raymond; Timothy X. Witkowski; Anthony P. Bottion

(57) ABSTRACT

A compound of Formula I or of Formula II

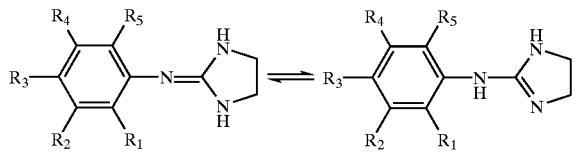

Formula I  Formula II wherein:

$R_1$ is F, Cl, Br, $CH_2F$, $CF_2H$, or $CF_3$;

$R_2$ is $NR_6R_7$, where $R_6$ is Me, Et, Pr, or iPr, and $R_7$ is Me, Et or Pr; and $R_3$, $R_4$, and $R_5$ independently of one another each are H, Me, F, Cl, Br, $CH_2F$, $CF_2H$, or $CF_3$, and if $R_4$ is Me, F, Cl, Br, $CH_2F$, $CF_2H$, or $CF_3$, then $R_1$ is additionally H or Me, or a pharmacologically acceptable salt thereof. In addition, pharmaceutical compositions comprising an effective amount of these compounds, methods for the treatment or prophylaxis of urinary incontinence and diseases of the bladder using these compounds, and methods for making these compounds are disclosed.

22 Claims, No Drawings

M-AMINO-PHENYLIMINO-IMIDAZOLIDINE DERIVATIVES FOR TREATING URINARY INCONTINENCE

RELATED APPLICATIONS

This application is a continuation of U.S. application Ser. No. 09/976,917, filed Oct. 12, 2001, now U.S. Pat. No. 6,602,879. Benefit under 35 U.S.C. §119(e) of prior U.S. provisional application Serial No. 60/248,172, filed Nov. 14, 2000, is hereby claimed. Both of these applications are hereby incorporated by reference in their entireties.

FIELD OF THE INVENTION

The present invention relates to m-amino-phenylimino-imidazolidine derivatives with a new pattern of substituents at the phenyl ring and the use of m-amino-phenylimino-imidazolidine derivatives for the preparation of pharmaceutical compositions, particularly for treating urinary incontinence, and processes for preparing them.

BACKGROUND OF THE INVENTION

The compounds described within the scope of the present invention belong to the category of the m-amino-phenylimino-imidazolidines. Similar compounds are known from the prior art.

Thus, for example, EP-A-0 236 636, inter alia, describes m-amino-phenylimino-imidazolidine derivatives with a primary amino function in the 3 position and their use as hemostatic agents. Clonidine derivatives of this kind are also discussed in EP-A-0 070 084, EP-A-0081923, EP-A-01 17102, EP-A-0 149 140, DE-A-2806811 or DE-A-2854659. Furthermore, U.S. Pat. No. 4,587,257 and EP-A-0081924 disclose m-amino-phenylimino-imidazolidine derivatives having a primary or acetylated amino function which can be used in ophthalmology. Biochem. Pharmacol. 32 (12) (1983), pp. 1933–1940, in another context discloses, inter alia, 2-(3-amino-2,6-dichlorophenylimino)imidazolidines. U.S. Pat. No. 4,287,201, for example, describes 2-(3-diethylamino-2-methylphenylimino)imidazolidines for increasing egg production in hens. Among others, WO 95/19968 discloses aminophenyliminoimidazole derivatives which are used as alpha 2 agonists in anesthesia, in the treatment of pain, high blood pressure, or hyperglycemia, or as soporifics.

WO 96/32939, which is hereby incorporated by reference in its entirety, discloses phenylimino-imidazoles, including those in which the phenyl ring has a primary or tertiary amine, an amide or imide in the meta position to the imino function. The compounds described therein count as alpha-1L-agonists and can advantageously be used in this capacity for treating urinary incontinence.

By incontinence is meant the involuntary release of urine, i.e., weakness of the bladder. The various forms of urinary incontinence include urge incontinence, reflex incontinence, overflow incontinence and stress or load incontinence. The most common forms of urinary incontinence include load incontinence or stress incontinence. These affect women in particular after more or less difficult childbirth. The reason for this is that pregnancy and childbirth can easily lead to weakening of the pelvic floor. Other causes of incontinence may be found, for example, in damage to the nerves of the pelvic floor, a congenitally short urinary tract or damage to the sphincter muscle.

The use of alpha-IL-agonists in the treatment of urinary incontinence is advantageous because they act selectively on the adrenoceptors of the bladder and thus exert a major influence on the tone of the ureter without significantly affecting the cardiovascular system.

In the prior art the possibility of using imidazole derivatives to treat incontinence has long been discussed. Surprisingly, there are opinions which indicate that many imidazole derivatives can counteract weakness of the bladder, whereas other authors have observed an apparently directly opposite effect, namely that substances of this kind can relieve obstruction of the bladder. Still other authors, talking about some of the same substances, report that they would have no effect at all on bladder function.

Thus, it is reported that alpha 2 agonists such as clonidine would have a positive effect on nocturnal incontinence (Urology, 43 (3) (1994), pp. 324–327). On the other hand, in respect of clonidine itself, there is the contrary observation that this substance might even promote incontinence (Clin. Biol. Res. 78 (1981), pp. 101–103) and a similar observation is expressed in Jpn. J. Pharmacol. 58 (4) (1992), pp. 339–346. The authors find that clonidine does not have a distinct influence on bladder function but that phenyl-ethanol-amines such as phenylephrine, midodrine or ST 1059, which are similar to adrenaline, and are all alpha 1 agonists, do have such an effect. EP-A-0 416 841 also deals with the influence of alpha agonists on bladder function. It describes how alpha 1 adrenoceptor-blocking substances could be used to treat obstruction of the bladder. The observations according to U.S. Pat. No. 4,226,773, also point in this direction. According to this specification, pyrazolyliminoimidazole derivatives can be used to promote the release of urine. Other alpha 1 adrenergic imidazoles such as thiophene-pyrroles, for example, may be used to treat urinary incontinence (EP-A-0 599 697).

These different observations from the prior art lead one to conclude that up till now it has been impossible to predict the influence of imidazole derivatives on bladder function.

SUMMARY OF THE INVENTION

Compounds which may be used to treat urinary incontinence not only have to be sufficiently effective but should also have as few side effects as possible. In other words, if possible they should act selectively on the bladder only. Undesirable side effects include, among other things, a negative effect on the cardiovascular system. For particularly effective treatment of urinary incontinence, the bioavailability of the substances and their metabolism are also of particular importance. The bioavailability should be as great as possible and the metabolism should be such that the substances are not broken down too rapidly on the one hand and no toxic compounds or other compounds having undesirable pharmacological properties in this context are formed on the other hand.

It is therefore an objective of the present invention to find new alpha-1L-agonists from the category of the phenyliminoimidazolidines which are identical or similar in their activity to the compounds known from the prior art, which act selectively on the bladder without substantially affecting the cardiovascular system and have enhanced qualities in terms of their bioavailability or metabolism.

Surprisingly, it has been found that the m-amino-phenylimino-imidazolidines according to the invention meet the objective of the present invention and are therefore particularly suitable for treating urinary incontinence. For the use of these compounds in connection with urinary incontinence it is essential on the one hand that the amino group is a tertiary amine and on the other hand that the other positions of the phenyl ring are substituted in a particular way.

DETAILED DESCRIPTION OF THE INVENTION

According to the invention, the m-amino-phenylimino-2-imidazolidine derivatives of general formula I are used for the preparation of medicaments for the treatment of urinary incontinence:

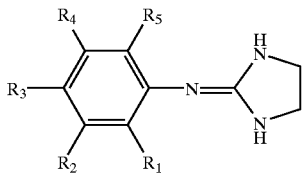

Formula I wherein:
  $R_1$ denotes F, Cl, Br, $CH_2F$, $CF_2H$, and/or $CF_3$;
  $R_2$ denotes $NR_6R_7$, where
    $R_6$ denotes Me, Et, Pr or iPr,
    $R_7$ denotes Me, Et or Pr; and
  $R_3$, $R_4$, and $R_5$ independently of one another each denote H, Me, F, Cl, Br, $CH_2F$, $CF_2H$ and/or $CF_3$, and, in the event that $R_4$ denotes Me, F, Cl, Br or $CF_3$, then $R_1$ additionally also denotes H or Me.

Me denotes methyl, $CF_3$ denotes trifluoromethyl, $CH_2F$ denotes fluoromethyl, $CF_2H$ denotes difluoromethyl, Et denotes ethyl, Pr denotes propyl, iPr denotes isopropyl, H denotes hydrogen, F denotes fluorine, Cl denotes chlorine, Br denotes bromine, and N represents nitrogen.

Of these compounds with the hereinbefore-given structural formula, compounds of formula I are preferred wherein:
  $R_1$ denotes F, Cl, Br, or $CF_3$;
  $R_2$ denotes $NR_6R_7$, where
    $R_6$ denotes Me or Et,
    $R_7$ denotes Me or Et; and
  $R_3$, $R_4$, and $R_5$ independently of one another each denote H, F, Cl, Br, and/or $CF_3$.

Also preferred are those compounds of formula I wherein $R_1$ may additionally also denote H or Me if $R_4$ is F, Cl, Br or $CF_3$.

Particularly preferred are compounds of formula I wherein:
  $R_1$ denotes Me;
  $R_2$ denotes $NR_6R_7$, where
    $R_6$ denotes Me or Et, preferably Me,
    $R_7$ denotes Me or Et, preferably Me;
  $R_3$ denotes H, F, Br or $CF_3$;
  $R_4$ denotes Cl, Br or $CF_3$; and
  $R_5$ denotes H, Br or $CF_3$,
  and/or if $R_1$ denotes Cl, Br or $CF_3$, then $R_4$ denotes H.

Of these, the most preferred are compounds of formula I wherein
  $R_1$ denotes Me;
  $R_2$ denotes $NR_6R_7$, where
    $R_6$ denotes Me,
    $R_7$ denotes Me;
  $R_3$ denotes H, F, preferably H;
  $R_4$ denotes Cl or Br; and
  $R_5$ denotes H or Br,
  and/or if $R_1$ denotes Cl or Br, then $R_4$ denotes H.

The compounds represented by formula I may be present in tautomeric equilibrium with the m-aminoanilino-2-imidazoline derivatives of formula II:

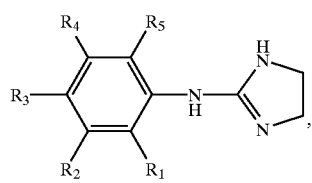

Formula II in which the definitions of the groups $R_1$, $R_2$, $R_3$, $R_4$, $R_5$, $R_6$, and $R_7$ are identical to the abovementioned compounds of formula I and all the preferences listed.

Therefore, the present invention also relates to the compounds which come under general formula II wherein the groups $R_1$, $R_2$, $R_3$, $R_4$, $R_5$, $R_6$, and $R_7$ fall within the scope of the definitions given under formula I. The same is true of the preferred ranges mentioned under formula I.

The compounds which fall within the scope of definitions of formulae I and II are equally preferred, but independently of one another.

With regard to the nomenclature used within the scope of the present invention, it should be pointed out that the term "phen-1'-yl-2-imidazolidine" denotes compounds having the following structural element:

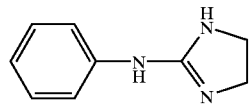

This means that the atoms of the imidazole ring are numbered 1, 2, 3, etc., with one nitrogen atom being numbered 1 and the other nitrogen atom being numbered 3. Consequently, the imino group is bound to the carbon atom, which is assigned the number 2. The atoms of the phenyl ring are numbered 1', 2', 3', etc., while the carbon atom of the phenyl ring which is bound to the imino group is designated 1' throughout.

It is expressly mentioned that the corresponding tautomers according to general formula II are also included, even when they are not specifically mentioned. The same is true of all the m-aminoanilino-2-imidazolidine derivatives mentioned in the context of the present invention.

As representatives of all the compounds which come under general formula I or formula II, some m-dialkylaminophen-1'-yl-2-imidazolidines are mentioned hereinafter by way of example.

2'-Bromo-3'-chloro-5'-dimethylamino-6'-methylphen-1'-yl-2-iminoimidazolidine 1, preferably in the form of the hydrochloride,

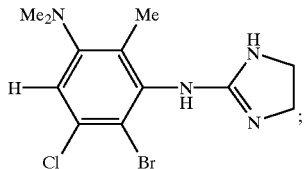

3'-bromo-5'-diethylamino-6'-methylphen-1'-yl-2-iminoimidazolidine 2, preferably in the form of the hydrochloride,

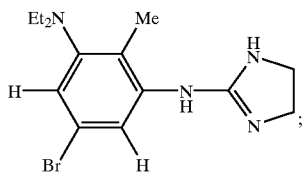

3'-bromo-5'-dimethylamino-6'-methylphen-1'-yl-2-iminoimidazolidine 3, preferably in the form of the free base,

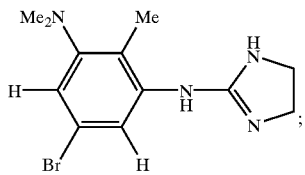

3'-chloro-5'-dimethylamino-6'-methylphen-1'-yl-2-iminoimidazolidine 4, preferably in the form of the hydrochloride,

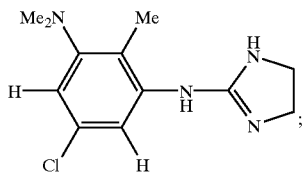

2'-3',-dibromo-5'-dimethylamino-6'-methylphen-1'-yl-2-iminoimidazolidine 5, preferably in the form of the free base

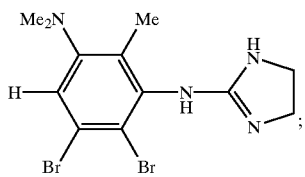

2'-chloro-3'-dimethylaminophen-1'-yl-2-iminoimidazolidine 6, preferably in the form of the free base

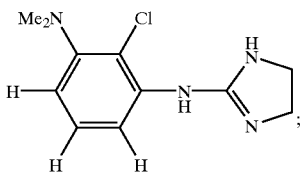

4'-bromo-2'-chloro-3'-dimethylaminophen-1'-yl-2-iminoimidazolidine 7, preferably in the form of the free base

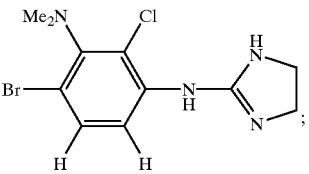

2'-bromo-6'-chloro-5'-dimethylaminophen-1'-yl-2-iminoimidazolidine 8,

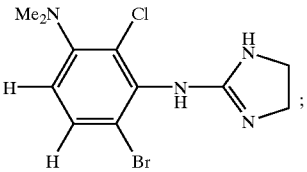

5'-bromo-2'-chloro-3'-dimethylaminophen-1'-yl-2-iminoimidazolidine 9;

2'-bromo-5'-dimethylamino-6'-fluorophen-1'-yl-2-iminoimidazolidine 10;

3'-chloro-6'-fluoro-5'-dimethylaminophen-1'-yl-2-iminoimidazolidine 11;

3'-chloro-4'-fluoro-5'-dimethylamino-6'-methylphen-1'-yl-2-iminoimidazolidine 12;

6'-chloro-3'-fluoro-5'-dimethylaminophen-1'-yl-2-iminoimidazolidine 13;

4'-chloro-3'-fluoro-5'-dimethylamino-6'-methylphen-1'-yl-2-iminoimidazolidine 14;

3'-6'-dichloro-5'-dimethylaminophen-1'-yl-2-iminoimidazolidine 15;

3'-4'-dichloro-5'-dimethylamino-6'-methylphen-1'-yl-2-iminoimidazolidine 16;

3'-4'-difluoro-5'-dimethylamino-6'-methylphen-1'-yl-2-iminoimidazolidine 17;

3'-6'-difluoro-5'-dimethylaminophen-1'-yl-2-iminoimidazolidine 18;

5'-dimethylamino-6'-methyl-2'-trifluoromethylphen-1'-yl-2-iminoimidazolidine 19; and 5'-dimethylamino-6'-methyl-3'-trifluoromethylphen-1'-yl-2-iminoimidazolidine 20.

Of these, the following are preferred:

2'-bromo-3'-chloro-5'-dimethylamino-6'-methylphen-1'-yl-2-iminoimidazolidine 1;

3'-bromo-5'-diethylamino-6'-methylphen-1'-yl-2-iminoimidazolidine 2;

3'-bromo-5'-dimethylamino-6'-methylphen-1'-yl-2-iminoimidazolidine 3;

3'-chloro-5'-dimethylamino-6'-methylphen-1'-yl-2-iminoimidazolidine 4;

2'-3'-dibromo-5'-dimethylamino-6'-methylphen-1'-yl-2-iminoimidazolidine 5;

2'-chloro-3'-dimethylaminophen-1'-yl-2-iminoimidazolidine 6;

4'-bromo-2'-chloro-3'-dimethylaminophen-1'-yl-2-iminoimidazolidine 7;

2'-bromo-6'-chloro-5'-dimethylaminophen-1'-yl-2-iminoimidazolidine 8; and

5'-bromo-2'-chloro-3'-dimethylaminophen-1'-yl-2-iminoimidazolidine 9;

and the pharmacologically acceptable salts thereof, particularly the hydrochlorides.

The following are particularly preferred:

2'-bromo-3'-chloro-5'-dimethylamino-6'-methylphen-1'-yl-2-iminoimidazolidine 1;

3'-bromo-5'-dimethylamino-6'-methylphen-1'-yl-2-iminoimidazolidine 3;

3'-chloro-5'-dimethylamino-6'-methylphen-1'-yl-2-iminoimidazolidine 4; and

2'-3'-dibromo-5'-dimethylamino-6'-methylphen-1'-yl-2-iminoimidazolidine 5;

and the pharmacologically acceptable salts thereof, particularly the hydrochlorides.

Most preferred is 3'-chloro-5'-dimethylamino-6'-methylphen-1'-yl-2-iminoimidazolidine 4 and the pharmacologically acceptable salts thereof, particularly the hydrochloride.

Another aspect of the present invention relates to the compounds of the abovementioned general formulae I and/or II and the pharmacologically-compatible salts thereof with the groups $R_1$ to $R_5$ in all known definitions and pharmaceutical composition comprising the same.

Within the framework of the present invention, the definition of all named compounds is not only to include the free bases but also the respective pharmaceutically-acceptable acid addition salts. Acids suitable for this purpose may be both inorganic and organic by nature. Examples of suitable acids include: hydrochloric acid, hydrobromic acid, sulfuric acid, phosphoric acid, fumaric acid, citric acid, lactic acid, acetic acid, propionic acid, malic acid, succinic acid, amino acid, particularly glutamic acid or aspartic acid, carbohydrate acids and acids derived from carbohydrate. Salts of this kind may be important for galenic preparations both for increasing the stability, especially the long-term stability of the compounds and/or for increasing the bioavailability. Hydrochloride salts are preferred, either the monohydrochlorides or dihydrochlorides, depending on the particular compound. The same is true of the preferred compounds.

As already described hereinbefore, within the framework of the present invention the abovementioned compounds are distinguished over the compounds known from the prior art by their pharmacological properties, particularly with regard to their bioavailability and/or metabolism. It goes without saying that the most preferred compounds are those which have a high level of activity and bioavailability and a low metabolic breakdown. Another feature which is crucial when selecting particularly suitable compounds for treating urinary incontinence is the selectivity with which the compound in question acts on bladder function without seriously affecting other bodily functions, particularly the cardiovascular system.

Within the framework of the present invention, the named compounds and their pharmacologically-compatible acid addition salts can be prepared in suitable pharmaceutical formulations. This includes all formulations capable of being used medicinally. These are, for example, solutions, suspensions, aerosols, powders, tablets, coated tablets, suppositories, creams, etc.

The compounds according to the invention, the pharmacologically acceptable acid addition salts thereof and/or pharmaceutical preparations containing them may be used medicinally for treating diseases, especially diseases of the bladder, particularly in urinary incontinence. The compounds according to the invention are most preferably used for treating stress incontinence.

According to another aspect, the present invention relates to processes for preparing the abovementioned compounds, the pharmacologically acceptable acid addition salts and/or pharmaceutical preparations thereof, and the use of the compound described for preparing other pharmacologically active derivatives thereof.

EXAMPLES

1. Bioavailability

In order to determine bioavailability, the test substances were administered orally to a group of 8 male rats which had been fasted. As a comparison, the test substances were administered intravenously to animals in an identical second group. 1 ml blood samples were taken from the animals of both groups at specified times after administration (10 minutes, 30 minutes, 1 hour, 2 hours, and 4 hours, and additionally after 6 hours in the case of the animals treated by oral route). The blood samples taken in each group were mixed together (8 ml). After further working up, the content of the test substances in the blood for the particular time was determined from the plasma by HPLC (High Performance Liquid Chromatography) using standard methods and compared for the two groups.

Results

| Compound | Bioavailability |
| --- | --- |
| 4, hydrochloride | 11% |
| 5, dihydrochloride | 0.8% |

2. Metabolism

To determine the metabolism, the enzyme CYP2D6 was allowed to act on the test substances. After 30 minutes, a check was made to see how much of the test substance put in had been broken down by the enzyme.

The rate of breakdown under the effect of the enzyme HLM/60 minutes is tested analogously.

| Compound | % Breakdown of Substrate after 30 minutes' Incubation with CYP2D6 | Breakdown of Substrate after 60 minutes' Incubation with HLM |
| --- | --- | --- |
| 1, hydrochloride | 40.5 | 32.1 |
| 3, base | 33.9 | 17.0 |
| 4, hydrochloride | 36.5 | 17.1 |
| 5, dihydrochloride | 22.2 | 22.0 |

-continued

| Compound | % Breakdown of Substrate after 30 minutes' Incubation with CYP2D6 | Breakdown of Substrate after 60 minutes' Incubation with HLM |
|---|---|---|
| 6 base | — | 7.4 |
| 7 base | 46.4 | 55.8 |

3. Efficacy and Selectivity

The efficacy and selectivity of the compounds is determined as follows:

| Compound | Activity in the Dog | Activity on Human Urethra | Selectivity in the Dog |
|---|---|---|---|
| 1, in the form of the hydrochloride | 109 | 100 | 0.92 |
| 3, in the form of the base | 87 | 72 | 0.76 |
| 4, in the form of the hydrochloride | 116 | 137 | 0.99 |
| 5, in the form of the dihydrochloride | 89 | 113 | 0.71 |

The maximum contraction in the dog and the activity on the human urethra are given as percentages of contraction compared with noradrenalin. Selectivity in the dog: percentage contraction on the femoral artery in the dog at $10^{-5}$ M—percentage contraction on the carotid artery in the dog at $10^{-5}$ M.

4. Preparation

The compounds according to the invention may be prepared as described in WO 96/32939 on pages 11 to 16, to which reference is hereby expressly made. Some of the compounds according to the invention may be prepared, for example, starting from the compounds described therein, particularly the 2'-bromo-5'-dimethylamino-6'-methylphen-1'-yl-2-iminoimidazolidine described on page 16.

PREPARATION EXAMPLES

Compound 1
2'-Bromo-3'-chloro-5'-dimethylamino-6'-methylphen-1'-yl-2-iminoimidazolidine 1

2 g of 2'-bromo-5'-dimethylamino-6'-methylphen-1'-yl-2-iminoimidazolidine is dissolved at 0° C. in 6.7 ml of sulfuric acid and combined with 0.8 g of 1,3-dichloro-5,5-dimethylhydantoin with stirring. The solution is heated to 55° C. then, after 3 days, diluted with ice, made alkaline with $NH_4OH$ and extracted with ethyl acetate. The ethyl acetate extract is concentrated by evaporation under reduced pressure and the residue remaining is worked up by chromatography (silica gel, eluant: $CH_2Cl_2$/methanol/concentrated $NH_4OH$ (90/10/1)). 1.1 g of 2'-bromo-3'-chloro-5'-dimethylamino-6'-methylphen-1'-yl-2-iminoimidazolidine 1 is obtained as a white powder, melting point 239° C.–240° C. $^1$H NMR (250 MHz, $CD_3OD$, TMS=0 ppm): δ=8.09 (1H, s, aryl-H); 3.81 (4H, s, imidazolidine-$CH_2$—); 3.27(6H, s, $N(CH_3)_2$); 2.51 (3H, s, aryl-$CH_3$); exchangeable H under the solvent peak 4.88 ppm. MS m/z 331/333/335 (87/100/42).

Compound 3
3'-Bromo-5'-dimethylamino-6'-methylphen-1'-yl-2-iminoimidazolidine 3

Step 1

84 g of 2-methyl-3-nitroaniline is dissolved in 550 ml of THF. 53 ml of acetic anhydride is slowly added dropwise and the mixture is then stirred at 70° C. After about 1 hour, THF is distilled off and the residue is combined with 250 ml of petroleum ether. The solid precipitate is filtered off and dried at 50° C. 106 g of N-acetyl-2-methyl-3-nitroaniline is obtained as a light brown powder.

Step 2

106 g of N-acetyl-2-methyl-3-nitroaniline is dissolved in 500 ml of concentrated sulfuric acid. 93 g of 1,3-dibromo-5,5-dimethylhydantoin is added at RT and the mixture is stirred for about 24 hours at RT with the exclusion of light and for 2 hours at 50° C. 2.5 l of ice water is added and the crystals precipitated are filtered off, washed with water, and dried. 67 g of a mixture of N-acetyl-4-bromo-2-methyl-3-nitroaniline and N-acetyl-4,5-dibromo-2-methyl-3-nitroaniline is obtained as a white powder.

Step 3

67 g of the above mixture and 300 ml of HCl (32%) are dissolved in a mixture of 300 ml of methanol and 300 ml of THF and the solution is stirred at 90° C. After about 2 hours, the organic solvent is distilled off. The crystalline precipitate is suction filtered and washed with HCl (0.5 M) and water. The crystals are suspended in about 500 ml of water. The aqueous phase is made alkaline with solid $Na_2CO_3$ and extracted with about 400 ml of ether. The organic phase is filtered and concentrated by evaporation under reduced pressure. The residue is recrystallized from hot ether. 18 g of 4-bromo-2-methyl-3-nitroaniline is obtained as orange-yellow crystals. In addition, about 32 g of a mixture of 4-bromo-2-methyl-3-nitroaniline and 4,5-dibromo-2-methyl-3-nitroaniline are obtained as orange-yellow crystals.

Step 4

5.8 g of paraformaldehyde and 15 ml of formic acid are dissolved in 15 ml of DMF and heated to 90° C.–100° C. A solution of 18 g of 4-bromo-2-methyl-3-nitroaniline in 15 ml of DMF is added dropwise within 10 minutes. After 2hours, the mixture is added to about 600 ml of ice water and the aqueous phase is extracted with 300 ml of ether. The organic phase is washed with $Na_2CO_3$ (1M), filtered and evaporated down. The product is purified by chromatography (silica gel, eluant: petroleum ether/ethyl acetate (40/60). 15 g of N,N-dimethyl-4-bromo-2-methyl-3-nitroaniline is obtained as a brownish-orange oil.

Step 5

15 g of N,N-dimethyl-4-bromo-2-methyl-3-nitroaniline is dissolved in about 200 ml of THF and hydrogenated at 20° C. under 5bars pressure of hydrogen using Raney nickel as catalyst. 12 g of 2-bromo-5-dimethylamino-6-methylaniline is obtained as a brown oil.

Step 6

2.4 g of 2-bromo-5-dimethylamino-6-methylaniline and 3.2 g of N-acetyl-2-methylthioimidazolidinone are dissolved in 50 ml of ethanol at ambient temperature and the solution is refluxed. After about 6 hours, the solvent is evaporated and the oily residue is crystallized from about 50 ml of ethyl acetate. 2.5 g of 3'-bromo-5'-dimethylamino-6'-methylphen-1'-yl-2-iminoimidazolidine 3is obtained as a white powder, melting point 140° C.–143° C. $^1$H NMR (250 MHz, $CDCl_3$, TMS=0 ppm): δ=6.80 (2H, s, aryl-H); 4.39 (2H, s, broad, NH); 3.49 (4H, s, imidazolidine-$CH_2$—); 2.66 (6H, s, $N(CH_3)_2$); 2.10 (3H, s, aryl-$CH_3$). MS m/z 297/299 (100/100).

Compound 4
3'-Chloro-5'-dimethylamino-6'--methylphen-1'-yl-2-iminoimidazolidine 4

0.37 g of 2'-bromo-3'-chloro-5'-dimethylamino-6'-methylphen-1-yl-2-iminoimidazolidine, 0.350 mg of zinc powder, and 2 ml of HCl (10%) are dissolved in 10 ml of ethanol and refluxed. After 1 hour, the reaction mixture is filtered and the solvent is distilled off. The residue is treated with $Na_2CO_3$ (1M) while cooling and the product is extracted with ether. The ether extract is concentrated by evaporation under reduced pressure. The residue remaining is taken up in methanol and acidified with HCl. 0.2 g of 3'-chloro-5'-dimethylamino-6'-methylphen-1'-yl-2-iminoimidazolidine 4 (HCl) is Zobtained as a (hygroscopic) white powder. $^1$H NMR (250 MHz, $CD_3OD$, TMS=0 ppm): δ=7.93; 7.60 (2H, 2d (J=1.8 Hz), aryl-H); 3.80 (4H, s, imidazolidine-$CH_2$—); 3.31 (6H, s, $N(CH_3)_2$); 2.45 (3H, s, aryl-$CH_3$); exchangeable H under the solvent peak 4.88 ppm. MS m/z 253/255(100/43).

Compound 5
2', 3'-Dibromo-5'-dimethylamino-6'-methylphen-1'-yl-2-iminoimidazolidine 5

Steps 1, 2, 3, and 5 are analogous to those of the synthesis of compound 3

Step 4
3.6 g of a mixture of 4-bromo-2-methyl-3-nitroaniline and 4,5-dibromo-2-methyl-3-nitroaniline are reacted as in Example 3, Step 4. The product is purified by chromatography (silica gel, eluant: cyclohexane/ethyl acetate (90/10). 1.9 g of N,N-dimethyl-4,5-dibromo-2-methyl-3-nitroaniline is obtained as a yellow powder.

Step 6
0.9 g of 2,3-dibromo-5-dimethylamino-6-methylaniline and 0.4 g of N-acetyl-2-imidazolidinone are dissolved at RT in 8 ml of $POCl_3$ and the solution is stirred at 85° C. After about 8 hours, the solvent is evaporated off and the residue is combined with 100 ml of water. The aqueous phase is extracted with ethyl acetate and the organic phase is made alkaline with $Na_2CO_3$, filtered and evaporated down. The product is purified by chromatography (silica gel, eluant: ethyl acetate). 0.7 g of N-acetyl-2',3'-dibromo-5'-dimethylamino-6'-methylphenyl-2-iminoimidazolidine is obtained as a white powder.

Step 7
0.7 g of N-acetyl-2',3'-dibromo-5'-dimethylamino-6'-methylphenyl-2-iminoimidazolidine is refluxed in 60 ml of methanol. After 7 hours, the solvent is evaporated. The residue is dissolved in $CH_2Cl_2$ and acidified with HCl (4 N) (pH 1). The crystals precipitated are suction filtered, washed with ether, and dried. 0.68 g of 2',3'-dibromo-5'-dimethylamino-6'-methylphen-1'-yl-2-iminoimidazolidine 5 is obtained as a white powder (melting point from 240° C., decomposition). $^1$H NMR (250 MHz, $CD_3OD$, TMS=0 ppm): δ=8.19(1H, s, aryl-H); 3.81 (4H, s, imidazolidine-$CH_2$—); 3.26 (6H, s, $N(CH_3)_2$); 2.48 (3H, s, aryl-$CH_3$); exchangeable H under the solvent peak 4.89 ppm. MS m/z 375/377/379 (66/100/66).

Compound 6
2'-Chloro-3'-dimethylaminophen-1'-yl-2-iminoimidazolidine 6

Step 1
25 g of N,N-dimethyl-3-nitroaniline is dissolved in 225 ml of DMF. 20 g of N-chlorosuccinimide dissolved in 190 ml of DMF is slowly added dropwise and the solution is stirred at RT. After 24 hours, the solvent is evaporated. About 500 ml of ice is added to the red residue. The suspension is extracted three times with about 200 ml of diethylether. The ether phases are dried over $Na_2SO_4$, filtered, and evaporated down. 30.4 g of N,N-dimethyl-2-chloro-3-nitroaniline is obtained as a red oil. The crude product is used further without any additional purification.

Step 2
30.4 g of N,N-dimethyl-2-chloro-3-nitroaniline is dissolved in about 300 ml of MeOH and hydrogenated at 20° C. and 5bars pressure of hydrogen using Raney nickel as catalyst. The solvent is evaporated down and the product is purified by chromatography (silica gel, eluant: petroleum ether/ethyl acetate (3/1)). 12.8 g of 2-chloro-3-dimethylaminoaniline is obtained as a brown oil.

Step 3
4.4 g of 2-chloro-3-dimethylaminoaniline, 3.35 g of N-acetylimidazolidine, and 30.5 ml of $POCl_3$ are mixed together and stirred at RT. After 12 hours, the $POCl_3$ is distilled off and the residue is added to ice. The aqueous phase is made alkaline with a concentrated $NH_3$ solution and extracted twice with 200 ml of methylene chloride. The organic phases are dried, filtered, and evaporated down. 6.2 g of 2'-chloro-3'-dimethylaminophen-1'-yl-1-acetyl-2-iminoimidazolidine is obtained as a yellow oil. The crude product is refluxed in methanol. After 2 hours, the solvent is evaporated off. The residue is dissolved in diethylether in an ultrasound bath. The yellow crystals precipitated are suction filtered, washed, and dried. 2.2 g of 2'-chloro-3'-dimethylaminophen-1'-yl-1-acetyl-2-iminoimidazolidine 6 is obtained as a white powder, melting point 146° C.–148° C. $^1$H NMR (250 MHz, $CD_3OD$, TMS=0 ppm): δ=7.11 (1H, t, J=7.9 Hz, aryl-H(5)); 6.83; 6.74 (2H,2dd, J=7.9; 1.5 Hz, aryl-H(4/6)); 3.45 (4H, s, imidazolidine-$CH_2$—); 3.73(6H, s, $N(CH_3)_2$). MS m/z 239/241(100/46).

Compound 7
4'-Bromo-2'-chloro-3'-dimethylaminophen-1'-yl-2-iminoimidazolidine 7

1 g of 2'-chloro-3'-dimethylaminophen-1'-yl-1-acetyl-2-iminoimidazolidine is dissolved in 10 ml of DMF and the mixture is cooled to 0° C. A solution of 0.75 g of N-bromosuccinimide in 4.5 ml of DMF is slowly added dropwise and the resulting mixture is stirred at 0° C. After 5 hours, 60 ml of water is added. The aqueous phase is extracted three times with 50 ml of ethyl ether. The organic phases are dried, filtered, and evaporated down. The product is purified by chromatography (silica gel, eluant: $CH_2Cl_2$/MeOH/concentrated $NH_4OH$ (90/10/1)). 0.14 g of 4'-bromo-2'-chloro-3'-dimethylaminophen-1'-yl-2-iminoimidazolidine 7is obtained as a yellow powder, melting point 150° C.–155° C. $^1$H NMR (400 MHz, DMSO-$d_6$, TMS=0 ppm): δ=7.23; 6.54 (2H, 2d, J=8.6 Hz, 2aryl-H); 5.77 (2H, s, broad, NH); 3.28 (4H, s, imidazolidine-$CH_2$—); 2.58 (6H, s, $N(CH_3)_2$). MS m/z 317/319/321 (85/100/36).

Compound 8
2'-Bromo-6'-chloro-5'-dimethylaminophen-1'-yl-2-iminoimidazolidine 8

Steps 1 and 2are carried out as described for compound 6

Step 3
12.8 g of 2-chloro-3-dimethylaminoaniline is dissolved in 180 ml of DMF and stirred at 0° C. A solution of 13.4 g of N-bromosuccinimide in 80 ml of DMF is slowly added dropwise, so that the temperature does not rise above 2° C. The mixture is stirred for 5 hours at 0° C. and then at RT. After 48 hours, 700 ml of ice-water is added. The white precipitate is filtered off and the aqueous phase is extracted three times with 200 ml of diethyl ether. The organic phases are dried, filtered, and evaporated down. 17.5 g of 2-bromo-6-chloro-5-dimethylaminoaniline is obtained as a brown oil and used further without any additional purification.

Step 4

6.6 g of KSCN is dissolved in 220 ml of acetone at 10° C. 8 ml of benzoyl chloride is added. The solution is refluxed for 10 minutes and then cooled to 10° C. A solution of 17.5 g of 2-bromo-6-chloro-5-dimethylaminoaniline in 150 ml of acetone is slowly added dropwise. The mixture is refluxed. After 3 hours, 500 ml of ice water is added and the aqueous phase is extracted three times with 100 ml of ethyl acetate. The organic phases are dried, filtered, and evaporated down. The residue is dissolved in 150 ml of ethanol and refluxed with 39 ml of aqueous KOH (50%). After 2 hours, the solvent is distilled off. 15 g of N-thioamido-2-bromo-6-chloro-5-dimethylaminoaniline is obtained and used further without any additional purification.

Step 5

15 g of N-thioamido-2-bromo-6-chloro-5-dimethylaminoaniline and 4.6 ml of methyl iodide are stirred into 280 ml of methanol under reflux. After 2 hours, the solvent is evaporated off. 18.9 g of an orange-colored oil is obtained which is refluxed with 3.1 ml of ethylenediamine in 190 ml of acetonitrile. After 18 hours, the solvent is distilled off. The residue is combined with 110 ml of HCl (1 M) and extracted with ethyl ether. The organic phase is dried, filtered and evaporated down. The product is purified by chromatography (silica gel, eluant: $CH_2Cl_2$/MeOH/concentrated $NH_4OH$ (90/10/1)). 2.5 g of 2'-bromo-6'-chloro-5'-dimethylaminophen-1'-yl-2-iminoimidazolidine 8 is obtained as a pink powder, melting point 142° C.–145° C. $^1$H NMR (250 MHz, $CDCl_3$, TMS=0 ppm): δ=7.30 (1H, d, J=9.2 Hz, aryl-H(5)); 6.74(1H, d, J=9.2 Hz, aryl-H(4)); 3.98 (2H, s, broad, NH); 3.53(4H, s, imidazolidine-$CH_2$—); 2.87(6H, s, $N(CH_3)_2$). MS m/z 318/319/321(87/100/34).

Other compounds of the type described within the scope of this invention may be prepared analogously to the Examples provided above.

We claim:

1. A compound of Formula I or of Formula II

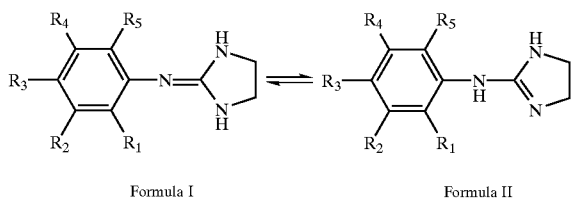

Formula I  Formula II wherein:

$R_1$ is F, Cl, Br, $CH_2F$, $CF_2H$, or $CF_3$;

$R_2$ is $NR_6R_7$, where $R_6$ is Me, Et, Pr, or iPr, and $R_7$ is Me, Et or Pr;

$R_3$ is Me, F, Cl, Br, $CH_2F$, $CF_2H$, or $CF_3$;

$R_4$ and $R_5$ are each independently H, Me, F, Cl, Br, $CH_2F$, $CF_2H$, or $CF_3$, and if $R_4$ is Me, F, Cl, Br, $CH_2F$, $CF_2H$, or $CF_3$, then $R_1$ is additionally H or Me, or a pharmacologically acceptable salt thereof.

2. A compound of Formula I or of Formula II

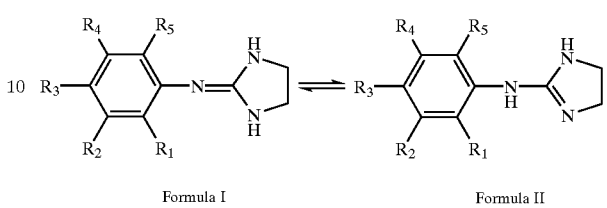

Formula I  Formula II wherein:

$R_1$ is H, Me, F, Cl, Br, $CH_2F$, $CF_2H$, or $CF_3$;

$R_2$ is $NR_6R_7$, where $R_6$ is Me, Et, Pr, or iPr, and $R_7$ is Me, Et or Pr;

$R_3$ and $R_5$ are each independently H, Me, F, Cl, Br, $CH_2F$, $CF_2H$, or $CF_3$; and $R_4$ is Me, F, Cl, Br, $CH_2F$, $CF_2H$, or $CF_3$; or a pharmacologically acceptable salt thereof.

3. A compound of Formula I or of Formula II

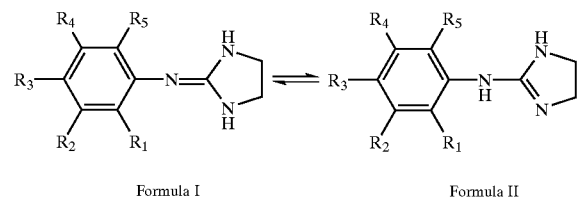

Formula I  Formula II wherein:

$R_1$ is H, Me, F, Cl, Br, $CH_2F$, $CF_2H$, or $CF_3$;

$R_2$ is $NR_6R_7$, where $R_6$ is Me, Et, Pr, or iPr, and $R_7$ is Me, Et or Pr;

$R_3$ and $R_4$ are each independently Me, F, Cl, Br, $CH_2F$, $CF_2H$, or $CF_3$;

$R_5$ is H, Me, F, Cl, Br, $CH_2F$, $CF_2H$, or $CF_3$, or a pharmacologically acceptable salt thereof.

4. A compound of Formula I or of Formula II

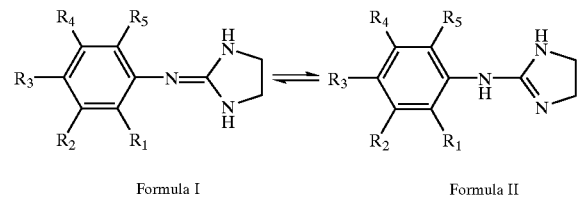

Formula I  Formula II wherein:

$R_1$ is H, Me, F, Cl, Br, $CH_2F$, $CF_2H$, or $CF_3$;

$R_2$ is $NR_6R_7$, where $R_6$ is Me, Et, Pr, or iPr, and $R_7$ is Me, Et or Pr;

$R_3$ is H, Me, F, Cl, Br, $CH_2F$, $CF_2H$, or $CF_3$; and $R_4$ and $R_5$ are each independently Me, F, Cl, Br, $CH_2F$, $CF_2H$, or $CF_3$;

or a pharmacologically acceptable salt thereof.

5. A compound of Formula I or of Formula II

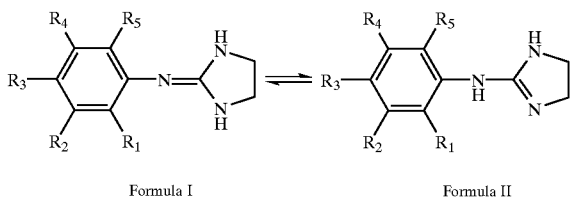

Formula I      Formula II wherein:
$R_1$ is H, Me, F, Cl, Br, $CH_2F$, $CF_2H$, or $CE_3$;
$R_2$ is $NR_6R_7$, where $R_6$ is Me, Et, Pr, or iPr, and $R_7$ is Me, Et or Pr;
$R_3$ and $R_5$ are each independently Me, F, Cl, Br, $CH_2F$, $CF_2H$, or $CF_3$; and
$R_4$ is H, Me, F, Cl, Br, $CH_2F$, $CF_2H$, or $CF_3$, and if $R_4$ is Me, F, Cl, Br, $CH_2F$, $CF_2H$, or $CE_3$, then $R_1$ is additionally H or Me,
or a pharmacologically acceptable salt thereof.

6. A compound of Formula I or of Formula II

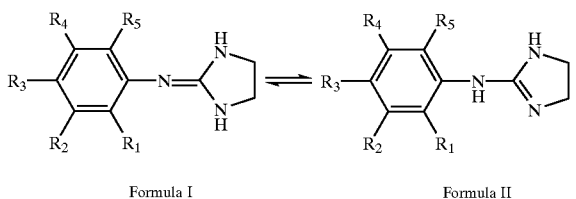

Formula I      Formula II wherein:
$R_1$ is H, Me, F, Cl, Br, $CH_2F$, $CF_2H$, or $CE_3$;
$R_2$ is $NR_6R_7$, where $R_6$ is Me, Et, Pr, or iPr, and $R_7$ is Me, Et or Pr; and
$R_3$, $R_4$, and $R_5$ are each independently Me, F, Cl, Br, $CH_2F$, $CF_2H$, or $CE_3$,
or a pharmacologically acceptable salt thereof.

7. A compound of Formula I or of Formula II

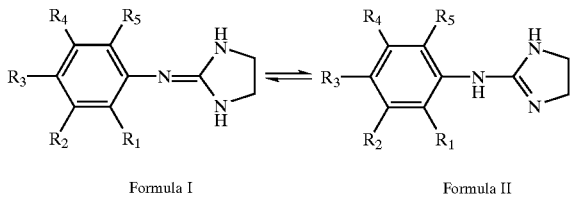

Formula I      Formula II wherein:
$R_1$ is H, Me, F, Cl, Br, or $CF_3$;
$R_2$ is $NR_6R_7$;
$R_3$ and $R_5$ are each independently H, F, Cl, Br, or $CF_3$;
$R_4$ is F, Cl, Br, or $CF_3$; and
$R_6$ and $R_7$ are each independently Me or Et.

8. The compound according to claim 7, wherein:
$R_1$ is Me; $R_3$ is H, F, Br, or $CF_3$;
$R_4$ is Cl, Br, or $CF_3$; and
$R_5$ is H, Br, or $CF_3$.

9. The compound according to claim 8, wherein:
$R_1$, $R_6$, and $R_7$ are each Me;
$R_3$ is H or F;
$R_4$ is Cl or Br; and
$R_5$ is H or Br.

10. The compound according to claim 7, wherein:
$R_1$ is F, Cl, Br, or $CF_3$;
$R_3$, $R_4$, and $R_5$ are each independently H, F, Cl, Br, or $CF_3$; and
$R_6$ and $R_1$ are each independently Me or Et.

11. The compound according to claim 7, wherein:
$R_1$ is Cl, Br, or $CF_3$;
$R_3$ is H, F, Br, or $CF_3$; and
$R_5$ is H, Br, or $CF_3$.

12. The compound according to claim 7, wherein:
$R_1$ is Cl or Br;
$R_3$ is H or F;
$R_5$ is H or Br;
$R_6$ and $R_7$ are each Me.

13. A compound selected from the group consisting of:
(a) 2'-bromo-3'-chloro-5'-dimethylamino-6'-methylphen-1'-yl-2-iminoimidazolidine;
(b) 3'-bromo-5'-dimethylamino-6'-methylphen-1'-yl-2-iminoimidazolidine;
(c) 3'-bromo-5'-dimethylamino-6'-methylphen-1'-yl-2-iminoimidazolidine;
(d) 3'-chloro-5'-dimethylamino-6'-methylphen-1'-yl-2-iminoimidazolidine;
(e) 2'-3'-dibromo-5'-dimethylamino-6'-methylphen-1'-yl-2-iminoimidazolidine;
(f) 2'-chloro-3'-dimethylaminophen-1'-yl-2-iminoimidazolidine
(g) 4'-bromo-2'-chloro-3'-dimethylaminophen-1'-yl-2-iminoimidazolidine;
(h) 2'-bromo-6'-chloro-5'-dimethylaminophen-1'-yl-2-iminoimidazolidine; and
(i) 5'-bromo-2'-chloro-3'-dimethylaminophen-1'-yl-2-iminoimidazolidine,
or a tautomer thereof or a corresponding pharmacologically-compatible salt thereof.

14. A compound selected from the group consisting of:
(a) 2'-bromo-3'-chloro-5'-dimethylamino-6'-methylphen-1'-yl-2-iminoimidazolidine;
(b) 3'-bromo-5'-dimethylamino-6'-methylphen-1'-yl-2-iminoimidazolidine;
(c) 3'-chloro-5'-dimethylamino-6'-methylphen-1'-yl-2-iminoimidazolidine; and
(d) 2'-3'-dibromo-5'-dimethylamino-6'-methylphen-1'-yl-2-iminoimidazolidine;
or a tautomer thereof or a corresponding pharmacologically-compatible salt thereof.

15. 3'-chloro-5'-dimethylamino-6'-methylphen-1'-yl-2-iminiomidazolidine, or a tautomer thereof or a corresponding pharmacologically-compatible salt thereof.

16. 2'-chloro-3'-dimethylaminophen-1'-yl-2-iminoimidazolidine, or a tautomer thereof or a corresponding pharmacologically-compatible salt thereof.

17. 4'-bromo-2'-chloro-3'-dimethylaminophen-1'-yl-2-iminoimidazolidine, or a tautomer thereof or a corresponding pharmacologically-compatible salt thereof.

18. The compound of Formula I or of Formula II according to one of claims 1, 2, or 3, to 7, wherein the compound of Formula I or of Formula II is an imino-imidazolidine.

19. The compound of Formula I or of Formula II according to one of claims 1, 2, or 3, to 7, wherein the compound of Formula I or of Formula II is an amino-imidazoline.

20. A pharmaceutical composition comprising an effective amount of a compound of Formula I or of Formula II according to one of claims 1, 2, or 3, to 7, and an inert carrier or diluent.

21. A pharmaceutical composition comprising an effective amount of a compound of Formula I or of Formula II according to claim 18 and an inert carrier or diluent.

22. A pharmaceutical composition comprising an effective amount of a compound of Formula I or of Formula II according to claim 19 and an inert carrier or diluent.

* * * * *